United States Patent [19]
Harrell et al.

[11] Patent Number: 5,196,165
[45] Date of Patent: Mar. 23, 1993

[54] AIR BLEEDING APPARATUS FOR AN AUTOCLAVE

[75] Inventors: Duronnie L. Harrell; Ye Mu, both of Charlotte, N.C.

[73] Assignee: The Pelton & Crane Company, Charlotte, N.C.

[21] Appl. No.: 631,134

[22] Filed: Dec. 20, 1990

[51] Int. Cl.$^5$ .......................... G05B 19/00; A61L 2/06
[52] U.S. Cl. ........................................ 422/26; 422/108; 422/110; 422/116; 422/112
[58] Field of Search ................ 422/26, 108, 109, 110, 422/116, 3, 112; 364/551.01, 557, 558

[56] References Cited

U.S. PATENT DOCUMENTS

| | | | |
|---|---|---|---|
| 3,494,725 | 2/1970 | Irons et al. | 422/26 |
| 4,164,538 | 8/1979 | Young et al. | 422/26 |
| 4,203,947 | 5/1980 | Young et al. | 422/26 |
| 4,238,447 | 12/1980 | Wolff | 422/26 |
| 4,372,916 | 2/1983 | Chamberlain et al. | 422/26 |
| 4,759,909 | 7/1988 | Joslyn | 422/26 |
| 4,865,814 | 9/1989 | Childress | 422/109 |

Primary Examiner—James C. Housel
Assistant Examiner—Long V. Le
Attorney, Agent, or Firm—Lawrence C. Edelman

[57] ABSTRACT

A device for removing air from the steam chamber of an autoclave includes a sealable sterilization chamber for receiving items to be sterilized. The chamber is sealed and the pressure and temperature therein monitored by sensors. Vapor for sterilizing items is generated in the chamber by a heater. Air is removed from the chamber through a relatively large vent and a selectively activated valve for opening and closing the vent. A digital controller receives the monitored temperature and pressure of the chamber as inputs, compares these empirical values with standard values and, on the basis of the comparison, generates a control signal to selectively open or close the valve. The vapor used in steam and the standard values are a set of coordinates, which when plotted on a pressure/temperature graph, would yield a curve characteristic of saturated steam. The standard values are stored in a memory accessible to the microprocessor. Below a given chamber temperature, venting is discontinued whenever a saturated steam condition is sensed, and above a given chamber temperature, when saturated steam is consistently achieved, the pre-conditioning stage is ended. The entire process of pre-conditioning is controlled by the digital controller, preferably a programmed microprocessor. The time period between successive monitorings of the chamber temperature and pressure is shortened as the temperature in the steam chamber increases.

6 Claims, 1 Drawing Sheet

AIR BLEEDING APPARATUS FOR AN AUTOCLAVE

FIELD OF THE INVENTION

The present invention relates to an apparatus and method for bleeding air from the steam chamber of an autoclave, and more particularly to a microprocessor controlled air bleed apparatus and method which monitors the steam condition in the autoclave and performs controlled air evacuation according to the monitored values.

DESCRIPTION OF THE PRIOR ART

Steam at a temperature range of 120 to 135 degrees Celsius is generally required for effective sterilization and these temperature values are employed in an autoclave. There are numerous autoclave designs in the prior art. Each design must provide a means of introducing the objects to be sterilized into a steam pressure chamber, a means for resealing the chamber with the objects therein, and a means for introducing steam into the chamber at a desired temperature, pressure and for a duration of time to enable sterilization. Most autoclaves have a common operational requirement, namely, that air which has been inadvertently introduced into the steam chamber during the loading of the objects to be sterilized must be removed from the chamber. Air within an autoclave chamber acts as an insulator, insulating the occupied volume from the heat of the steam, rendering sterilization more difficult. It is therefore advantageous to have the maximum concentration of steam, "saturated steam", within the chamber with the minimum concentration of air. It is also desirable to remove the air from the chamber as quickly as possible to speed up the sterilization process and to promote an efficient use of heat energy. The operation of an autoclave involves a set of characteristic procedures, such as loading the steam chamber with the objects to be sterilized, pre-conditioning the chamber by removing air from the load and the chamber, providing saturated steam in the chamber, and sterilizing the load by maintaining the presence of saturated steam at a given temperature and pressure for a given period of time. In addition, the autoclave must be depressurized by the venting of steam after the sterilization is complete and prior to unloading, and frequently a drying stage is required to remove condensation from the load. The focus of the present invention, however, is the apparatus and method for the removal of air from the chamber, i.e., in the pre-conditioning stage, and the creation of a saturated steam environment in the chamber. There are essentially three basic methods for removing air from the chamber, i.e., (1) by evacuating the air from the chamber prior to introducing the steam charge — the "pre-vacuum method"; (2) by admitting steam into the chamber and, relying on the relative heaviness of the air, allowing a separation and stratification of the air and steam in the chamber to occur, the air assuming the lower position, then draining the lower air layer from the chamber — the "downward or gravity displacement"method; and (3) by repeated discharges of mixed steam and air to gradually reduce the concentration of air, followed by repressurization — the "pulse" method. In Linder U.S. Pat. No. 3,481,692 entitled ARRANGEMENT FOR A STEAM-HEATED AUTOCLAVE, issued Dec. 2, 1969, a pressure sensor detecting a pressure below a preset minimum activates the generation of steam that is introduced into an autoclave steam chamber. The chamber is vented through a selector valve which remains open when air is passing through it but closes when steam passes through the valve. Steam is continually fed to the chamber even after the selector valve is closed, leading to a rapid build-up of pressure. The pressure is allowed to build until reaching a preset maximum value, as sensed by the pressure sensor, at which point steam supply is curtailed. Although it is not perfectly clear from Linder, apparently, the steam charge and the air in the chamber stratify. The cooler air sinks to the bottom of the chamber where the vent conduit communicates with the chamber. In addition, Linder teaches that the selector valve should be cooled thus leading to an opening of the valve in the absence of a continual supply of steam. Thus, the stratified air is discharged out the vent conduit at the bottom of the chamber and through the selector valve. The decrease in pressure initiates another cycle of steam generation. This cyclic build-up and discharge is repeated until a maximum temperature is sensed by a thermostat located in the discharge conduit proximate the bottom of the chamber. When this occurs it is assumed that all the air is removed. The thermostat then controls the intermittent supply of steam to maintain the maximum temperature for a preset sterilization period as determined by the setting of a timer. Linder assumes that the entrapped air will be positioned near the thermostat and that the thermostat will not reach the maximum value until all air is removed from the chamber. Linder therefore employs a hybrid gravitational and pulse method. Depending upon the load, however, air may be trapped in or around the load thereby insulating the load. Even though the area near the thermostat indicates a temperature indicative of saturated steam, pockets of air may still remain in the chamber. Further, the cycling of the steam supply on to remove additional air depends upon the sensing and venting of air by the selector valve.

Irons U.S. Pat. No. 3,494,725 entitled PULSING PROCESS OF STERILIZATION, issued Feb. 10, 1970, is illustrative of a pure pulse method, in that, a chamber is loaded, sealed and steam admitted to the chamber under pressure. At predetermined timed intervals the steam and air mixture in the chamber is vented to the atmosphere, until a set minimum pressure is realized. At the predetermined minimum pressure point, the vent is closed and the chamber repressurized with steam. The pressurization, venting and repressurization is repeated until a predetermined temperature is reached within the chamber signalling the presence of saturated steam within the chamber. Once the signal temperature is reached, sterilization commences. As with the previously discussed designs, there is no assurance that monitoring the temperature at the location of the sensor indicates a complete absence of air throughout the chamber. In addition, the preset timed intervals of venting are not necessarily maximally efficient for each load. For example, for a load having a minimal amount of air, venting a smaller volume of steam/air during the pre-conditioning phase may be appropriate, whereas, for a load having a larger volume of air, or air positioned in pockets, a greater quantity may be required to be vented. The preset intervals of venting must assume worse case conditions, and therefor are wasteful with respect to efficient operation for less than worse case loads.

Joslyn U.S. Pat. No. 4,759,909 entitled METHODS AND APPARATUS FOR STEAM STERILIZATION, issued Jul. 26, 1988, relates to a hybrid pulse and gravity air removal method utilizing an air sensor in a vent line to sense when an environment of saturated steam is realized in the pressure chamber of an autoclave. Joslyn further incorporates a load temperature sensor, as well as, a chamber temperature sensor. Steam is admitted under pressure to the steam chamber until a preset maximum pressure is reached; the chamber is then vented through a drain conduit to the atmosphere. This infusion/venting or "pulsing" process is continued until either the load temperature sensor reading and the chamber temperature sensor readings converge, indicating that the load is saturated by steam, i.e., no layer of air insulates the load, or the air sensor in the vent line indicates that little or no air remains in the vent gases. While it would appear that a load temperature sensor remedies the problem of discounting pockets of air around the load, the sensor can only monitor one particular area of the load. While the temperature sensing of a two sensor system is better at determining the system temperature throughout the chamber, there are more than two locations in the chamber and therefore there is a good chance that air remaining in the chamber will be undetected.

In Childress U.S. Pat. No. 4,865,814 entitled AUTOMATIC STERILIZER, issued Sep. 12, 1989, and assigned to the assignee herein, a temperature sensitive bellows valve is in continuous contact with the contents of a steam chamber in which steam is created by means of an internal water heater. As well known, the bellows valve intermittently operates in response to temperature to vent the chamber. Childress also incorporates a high flow rate exhaust dump line controlled by a solenoid operated valve. The high flow dump line is opened when water is admitted to the steam chamber and into contact with the water heater to provide a pressure relief for the resultant rapid expansion of steam when incoming water contacts the heater. In the Childress device, intermittent venting occurs continuously during pre-conditioning and sterilization by means of the bellows valve. The bellows is temperature sensitive only at the tip, which, when the bellows is expanded and sealing the pressure chamber, is not exposed to the hot interior contents of the chamber. Rather, the temperature sensitive bellows tip is exposed only to the ambient temperature outside the chamber when the bellows valve is closed. Exposure to ambient air permits the tip to cool and the valve to open releasing a further quantity of steam from the chamber. As the steam passes over the bellows tip, it heats the tip, causing the valve to close. The orifice size of the bellows valve must be such that the rate of steam generation must greatly exceed the rate at which steam/air is vented when the valve is open, otherwise pressure would never build in the chamber and the steam passing over the tip would not be adequate to close the valve. Therefore, only small quantities of steam/air are expelled during each cycle of bellows valve opening/closing. This mode of operation is particularly effective when the load contains only small pockets of air, but when more sizeable quantities of air must be expelled from the load, the process consumes what can be considered excessive time and energy.

It is therefore an object of the present invention to provide a reliable means for rapidly and efficiently removing air from an autoclave as soon as possible in the pre-conditioning stage, irrespective of the amount of air entrained with the load.

It is a further object to provide a reliable means for ascertaining the degree of saturation of steam in an autoclave during the pre-conditioning stage.

SUMMARY OF THE INVENTION

The problems and disadvantages associated with the conventional techniques and devices utilized to remove air from the pressure chamber of an autoclave are overcome by the present invention which includes a sterilization chamber for receiving items to be sterilized. The chamber is sealed and the pressure and temperature therein are monitored by appropriate sensors. Steam for sterilizing items is generated in the chamber by a heater coupled to the chamber for converting water into steam. Air is removed from the chamber through a vent coupled to the chamber and a selectively activated valve coupled to the vent for opening and closing the vent. A digital controller controls the selectively activated valve. The controller receives the monitored temperature and pressure of the chamber as inputs, compares these empirical values with standard values and, on the basis of the comparison, generates a control signal to selectively open or close the valve.

BRIEF DESCRIPTION OF THE FIGURES

The sole figure in block form depicts an autoclave system in accordance with an exemplary embodiment of the present invention.

DETAILED DESCRIPTION OF THE FIGURES

Figure 1:
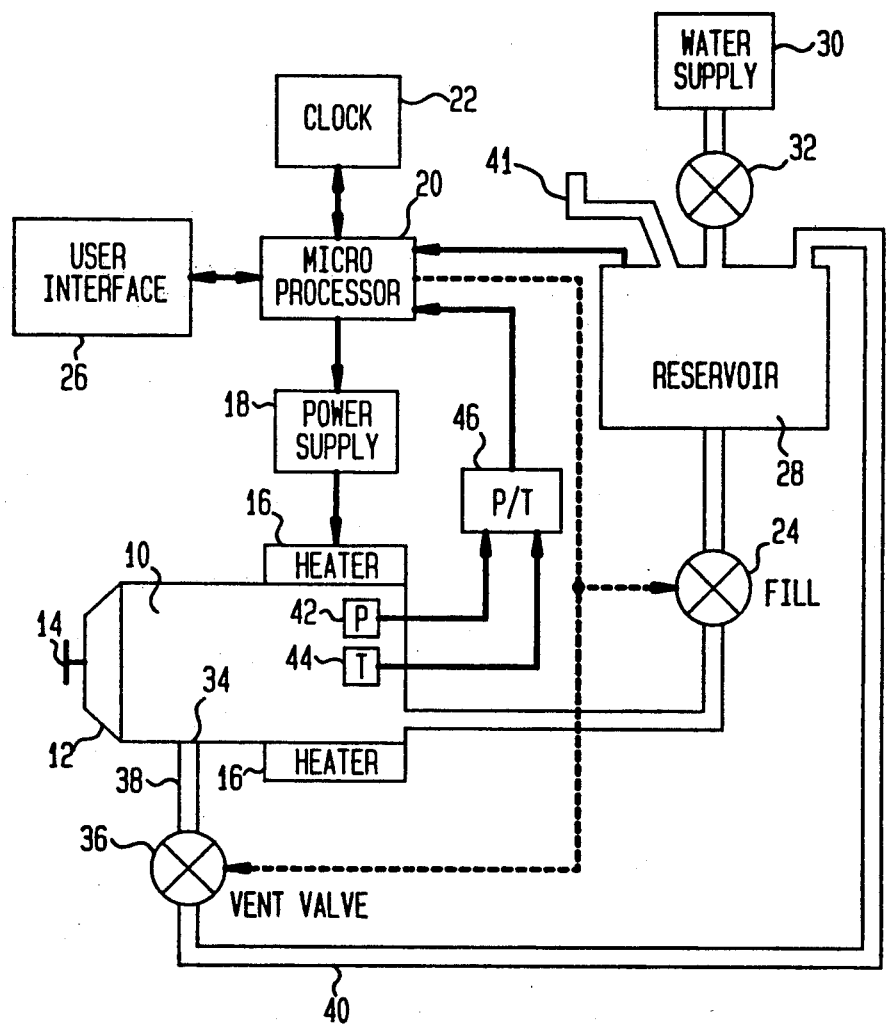

FIG. 1 shows a sterilizing pressure chamber 10 having a door 12 operated by a handle 14 for gaining access to the interior of the chamber 10 to place items to be sterilized therein. The chamber 10 is associated with a heater 16, which heater is supplied power by means of a power supply 18 under the control of a microcontroller or microprocessor module 20. The microprocessor module 20 includes or is associated with a clock 22. Clock 22, in cooperation with the microprocessor 20, controls the amount of water directed to the pressure chamber 10 by controlling the duration of opening of a fill valve 24. The microprocessor 20 is also associated with a user interface 26. The user interface 26 may consist of an LED or LCD display together with an input keypad to enable the user to set or select a particular mode or program of operation.

The fill valve 24 is coupled to an output port of a reservoir 28. The reservoir 28 contains a given amount of water which is supplied by means of a water supply 30 through a water supply valve 32. The reservoir feeds water into the chamber 10 by means of gravity when the fill valve 24 is opened. The water entering the chamber 10 may simply fall to the bottom of the chamber or be collected in a reservoir in the chamber, if such is provided, but in either event, the water must be pooled proximate the heater 16. The sterilization chamber 10 has vent orifice 34 preferably disposed towards the bottom of the chamber 10 which is coupled to a solenoid controlled vent valve 36, optionally, via a vent conduit 38. The microprocessor module 20 controls the operation of the solenoid and the state of the vent valve 36 as shall be described at length below. The output of the vent valve 36 is coupled to an output vent conduit 40 which empties into the reservoir 28. The reservoir 28 is vented to the atmosphere by vent 41 and thus comprises a pressure sink relative to the sealed chamber 10.

The venting passageway 40 may also include a coil (not shown) to condense steam in the passageway into water for return to the reservoir 28.

A pressure sensor 42 and a temperature sensor 44 are positioned within the chamber 10 to monitor the conditions therein. The respective pressure and temperature outputs are directed to a suitable analog to digital processing module 46 for converting the analog outputs of the sensors into digital signals which are received by the microprocessor 20.

In operation, the user selects, by entry of appropriate codes at the interface 26, an operating mode for the sterilizer as, for example, a preset time/temperature/pressure cycle for sterilizing a particular type and quantity of items which are placed inside the sterilization chamber 10. This information is directed to the microprocessor 20 which supplies the operating signals to implement the operation specified by the user. In the embodiment depicted, the system must first be supplied with a suitable quantity of water. This process is preferably performed in accordance with the process and by the apparatus described at length in application Ser. No. 07/590,270, filed Sep. 28, 1990, now U.S. Pat. No. 5,132,084 and entitled APPARATUS AND METHODS FOR DISPENSING WATER TO A STERILIZING CHAMBER OF AN AUTOCLAVE, by Duronnie Lee Harrell and Ye Mu, the applicants herein, and assigned to the assignee herein, which said application is copending with the present application.

Assuming that a suitable quantity of water is supplied to the pressure chamber, the pre-conditioning of the chamber, i.e., the establishment of an internal environment of saturated steam can then be started. The chamber 10 is first sealed. The solenoid controlled vent valve 36 is then opened, and the heater 16 turned on. Steam generation begins and the temperature and pressure signals from the sensors 42 and 44 are monitored. When the temperature inside the chamber reaches 98 degrees Centigrade, the solenoid controlled vent valve 36 is closed by a control signal from the microprocessor 20. The valve 36 remains closed until the temperature reaches 100 degrees Centigrade. At this time, the empirical temperature and pressure measurements from the chamber 10 are compared to the ideal saturated steam curve. The saturated steam curve is well known and available in many texts. The proper coordinates at given temperature and pressure intervals are stored as coordinates in a memory (not specifically shown) which memory may be part of the microprocessor 20 or external thereto. If the measured value pair can be matched to a pair of coordinates on the ideal curve within some acceptable range of tolerance, then the valve 36 remains closed. If the measurements do not indicate that saturated steam is present in the chamber 10, then the valve 36 is opened for 4 seconds, rapidly exhausting steam/air, then another measurement is taken. If this new measurement indicates a match, the valve 36 is closed, if not a match, the valve 36 remains open and the measurement is repeated 4 seconds later. This continues, with the valve opening or closing in response to each measurement, until the sensed temperature reaches 106 degrees Centigrade, at which time, the time interval between comparisons of the measured data to the stored ideal curve is shortened to 2 seconds and the opening or closing of the valve 36 depends upon the finding of a match, as before. Thus, saturated steam parameters are periodically checked between the temperatures of 100 to 111 degrees Centigrade. After 111 degrees Centigrade, when the readings consistently conform to those of saturated steam the valve 36 is closed, the pre-conditioning stage is complete and the sterilization stage can be started. This pre-conditioning method shortens the time required to obtain saturated steam within the chamber 10 and is particularly useful in cases where chamber loads have large air pockets. These benefits are realized in part by employing a larger size for vent orifice 34 than utilized in the air bellows of the previous apparatus. For example, vent orifice 34 should be at least twice as large as the orifice size in the typical prior art mechanical air bellows. The larger vent orifice 34 allows the unit to periodically rapidly exhaust air from the chamber and can achieve saturated steam conditions before the temperature gets close to the values required for sterilization, i.e., 121 to 132 degrees Centigrade.

An important advantage realized by the present invention is that the presence or absence of air during preconditioning within the chamber 10 can be determined reliably. This increased reliability is due to the simultaneous measurement of temperature and pressure and the comparison of this pair of values to the set of possible pairs comprising the coordinates making up the saturated steam curve. If the empirical pair cannot be found on the ideal curve within an acceptable degree of precision, then the chamber 10 does not contain saturated steam. Thus, even if a pocket of air is located in the chamber 10 beyond the sensory range of the temperature sensor 44, its presence will affect the pressure within the chamber 10 such that the pressure reading will not conform to the expected pressure of saturated steam at the temperature sensed by the temperature sensor 44.

Although any conventional sterilization and drying methods can be employed after the novel pre-conditioning procedure described above is completed, in the preferred embodiment, the operation of the sterilization and drying cycles of the sterilizer are as described in Bobby B. Childress U.S. Pat. No. 4,865,814 entitled AUTOMATIC STERILIZER and issued Sep. 12, 1989, and assigned to the same assignee as the present invention, and which is incorporated herein by reference.

Thus there has been shown and described a novel method and apparatus for creating a condition of saturated steam in the pressure chamber of an autoclave or, as this process is commonly termed in the art, "pre-conditioning" the chamber. Since the present invention accomplishes this pre-conditioning more quickly and efficiently than prior devices and processes, and insures that the process has been accomplished by sensing on a pair of values which together can not falsely indicate that the saturated steam condition exists when it does not, the invention fulfills the objects and advantages sought.

It should be understood that the embodiments described herein are merely exemplary and that a person skilled in the art may make many variations and modifications without departing from the spirit and scope of the invention as defined in the appended claims. For example, although in the described embodiment the valve is continuously held open during the time periods when it is determined that venting should occur, it may be desirable to operate the venting valve in a "pulse" manner, with a short intermittent closing during a time period when venting is supposed to occur, e.g., in order to avoid a "sticking" of the valve into an open or closed position. Furthermore, a vent valve may momentarily close at the end of a pressure/temperature measurement, and then be controlled to open or remain closed in response to the next sensed pressure/temperature. These and other modifications and variations are considered to be within the scope of the claims which follow.

We claim:

1. A sterilizing apparatus comprising:
    a sterilization chamber for receiving items to be sterilized;
    means coupled to said chamber for converting a fluid inside said chamber to sterilize said items during a sterilization cycle;
    means for monitoring temperature within said chamber;
    means for monitoring pressure within said chamber;
    a vent coupled to said chamber;
    a selectively activated valve coupled to said vent for opening and closing said vent during a preconditioning cycle before the start of said sterilization cycle, said vent enabling gases within said chamber to exit said chamber via said vent when said valve is open; and
    digital control means, including a memory having stored therein a plurality of different pressure and temperature values representative of a curve of related pressure and temperature values, for controlling said selectively activated valve during said preconditioning cycle, said control means receiving said monitored temperature and pressure as pairs of inputs and periodically comparing said pairs of inputs with said pressure and temperature values stored in said memory and on the basis of the comparison generating a control signal to selectively open or close said valve until one of said pairs of inputs first matches any one of said pairs of said pressure and temperature values stored in said memory, whereupon said valve remains closed and ending said preconditioning cycle.

2. The apparatus of claim 1, wherein said vent has a flow capacity therethrough when said selectively activated valve is open such that a greater volume of vapor can pass through said vent than can be formed by said converting means for any given period of time.

3. The apparatus of claim 1, wherein said control means receives said monitored temperature and pressure as inputs in a periodic manner.

4. The apparatus of claim 3, wherein the time period between successive inputs of said monitored temperature and pressure to said digital control means is initially a preset time duration, and as said monitored temperature within said chamber increases from an initial value, said time period between successive inputs of said monitored temperature and pressure is decreased from said preset time duration.

5. The apparatus of claim 4, wherein said digital control means includes a clock for timing the duration between successive inputs of the monitored temperature and pressure to said digital control means.

6. The apparatus of claim 4, wherein said vent is coupled to said chamber proximate a lower portion of said chamber such that said vent is a drain.

* * * * *